United States Patent [19]

Hatfield

[11] Patent Number: 5,779,980
[45] Date of Patent: Jul. 14, 1998

[54] GAS SENSOR HAVING A COMPOUNDED CATALYTIC STRUCTURE

[75] Inventor: Thomas N. Hatfield, Mishawaka, Ind.

[73] Assignee: CTS Corporation, Elkhart, Ind.

[21] Appl. No.: 783,858

[22] Filed: Jan. 16, 1997

[51] Int. Cl.$^6$ .................................................. G01N 27/16
[52] U.S. Cl. ...................... 422/95; 422/90; 422/94; 422/96; 422/97; 422/98; 73/31.06
[58] Field of Search ................. 422/90, 94–98; 73/31.06

[56] References Cited

U.S. PATENT DOCUMENTS

| Re. 33,980 | 6/1992 | Matsuura et al. | 422/98 |
|---|---|---|---|
| 3,564,474 | 2/1971 | Firth et al. | 422/97 X |
| 3,883,307 | 5/1975 | Kim | 422/97 |
| 3,959,764 | 5/1976 | Allman | 422/90 X |
| 4,045,177 | 8/1977 | McNally | 23/254 E |
| 4,164,539 | 8/1979 | Johnston | 422/97 X |
| 4,303,612 | 12/1981 | Sonley | 422/94 |
| 4,322,383 | 3/1982 | Yasuda et al. | 422/95 |
| 4,421,720 | 12/1983 | Kamiya et al. | 422/97 |
| 4,447,397 | 5/1984 | Anouchi et al. | 422/94 |
| 4,457,954 | 7/1984 | Dabill et al. | 422/98 X |
| 4,957,705 | 9/1990 | Uchikawa | 422/94 |
| 5,445,796 | 8/1995 | Mori | 422/98 |

FOREIGN PATENT DOCUMENTS

| 311964 | 4/1989 | European Pat. Off. | |
|---|---|---|---|
| 4001048 | 7/1991 | Germany. | |
| 52-49095 | 4/1977 | Japan. | |
| 54-36997 | 3/1979 | Japan. | |
| 54-139598 | 10/1979 | Japan. | |
| 54-139599 | 10/1979 | Japan. | |
| 55-65149 | 5/1980 | Japan. | |
| 55-126851 | 10/1980 | Japan. | |
| 55-149834 | 11/1980 | Japan. | |
| 58-196448 | 11/1983 | Japan. | |
| 63-128249 | 5/1988 | Japan. | |
| 1-119755 | 5/1989 | Japan | 422/98 |
| 1-265143 | 10/1989 | Japan. | |
| 1540212 | 2/1979 | United Kingdom. | |
| 2238617 | 6/1991 | United Kingdom. | |

*Primary Examiner*—Arlen Soderquist
*Attorney, Agent, or Firm*—Michael W. Starkweather; Daniel Tychonievich

[57] ABSTRACT

A gas sensor for detecting the presence of gases in air. In particular, sensors are described that have a compound catalytic support structure and are suitable for sensing hydrocarbons and nitrogen oxides. The device features a ceramic substrate having a temperature sensitive resistor on one surface. A mixture of ceramic particles and glass powder are applied over the substrate and resistor and fired so that the glass flows and adheres the ceramic particles to the substrate. A catalyst layer of either platinum or rhodium is deposited on the catalyst support and a thermally sensitive resistor element detects reactions of hydrocarbons or nitrogen oxides on the corresponding catalyst. The invention is suitable for sensing gases in the harsh environment of an automobile exhaust system.

29 Claims, 3 Drawing Sheets

GAS SENSOR HAVING A COMPOUNDED CATALYTIC STRUCTURE

BACKGROUND OF THE INVENTION

1. Field of the Invention

This invention relates to a sensor for detecting the presence of gases in air, and more specifically to a sensor having a compounded catalytic structure including a mixture of ceramic particles and glass both adhering to a base and resistor element.

2. Description of the Related Art

The use of catalysts to enhance the rate of chemical reactions is well known. A catalyst can be any substance that affects a chemical reaction rate without itself being consumed or undergoing a chemical change in the process. Catalysts may be inorganic, organic, or a complex composition of organic groups and metal halides.

The present invention is directed at the use of a catalyst in gas sensors. Catalytic gas sensors function by creating a chemical reaction when the gas to be sensed comes in contact with the catalyst. Often, the chemical reaction creates a temperature change that can be used to effect the electrical resistance of a juxtaposed conductor. Typical sensing elements are conductors whose conductivity varies according to temperature. Ordinarily, gas sensing devices include both a catalyzed sensor and a non-catalyzed reference sensor. Any difference in the sensor resistances is a result of the catalytic reaction from the ambient gas concentration. In other words, gas concentrations can be determined by measuring the difference in voltage across the catalyzed and non-catalyzed coated conductors.

3. Related Art

Examples of patents that are related to the present invention are as follows, and each patent is herein incorporated by reference for the supporting teachings:

U.S. Pat. No. 4,045,177, is an apparatus for detecting combustible gases.

U.S. Pat. No. 4,322,383, is a gas component detection device composed of two metal oxide sensors.

U.S. Pat. No. 4,447,397, is a catalytic gas sensor having a filament coated with titanium dioxide ($TiO_2$).

U.S. Pat. No. 4,957,705, is an oxygen gas concentration detecting device.

U.S. Pat. No. 5,445,796, is an oxygen concentrating sensor with a heat resistant coating.

U.S. Pat. No. Re. 33,980, is a thick film gas sensitive element.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singularly or when considered in combination, applicant's claimed invention.

4. Problems with Related Art

A problem with current gas sensors is that there are no compact, cost effective, and durable hydrocarbon or nitrogen oxide sensors that are suitable for functioning in the harsh environment of an automobile exhaust system. Sensors are needed to measure these gases to assure that automobiles are complying with emission requirements. Another problem is that current sensors use oxygen sensors that measure these gases indirectly, which is not as accurate as more direct measurement methods.

A further problem has been the difficulty in designing a sensor structure that will hold together under extreme temperature changes, vibrational effects, and exposure to contaminants without experiencing a significant degradation of performance over its expected life.

It is noted that the above described problems, and other problems are solved through the subject invention and will become more apparent to one skilled in the art, from the detailed description of the subject invention.

SUMMARY OF THE INVENTION

It is a feature of the invention to provide a gas sensor with a compounded catalytic structure for directly detecting the presence of gases in air. In particular, the sensor directly senses hydrocarbons or nitrogen oxides by using a thermally sensitive resistor that responds to an exothermic reaction of the gases on a catalyst.

An additional feature of the invention is to provide a device that is suitable for sensing gases in a harsh environment of an automobile exhaust system in a cost effective manner. The gas sensor disclosed meets these criteria by using a compounded catalytic structure that firmly adheres to the surface of the sensor and can be deposited using conventional thick film techniques.

A further feature of the invention is to provide a device with a structure that includes a ceramic base and resistor element located on the base. The electrical resistance of the resistor element changes as the temperature varies. A high surface area catalyst support structure comprising a mixture of glass and alumina particles is placed on top of the base and over the resistor element. A catalytic material is deposited on the catalytic support structure for creating an exothermic reaction of the gas to be sensed.

The invention resides not in any one of these features per se, but rather in the particular combination of all of them herein disclosed and claimed, and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Figure 1:
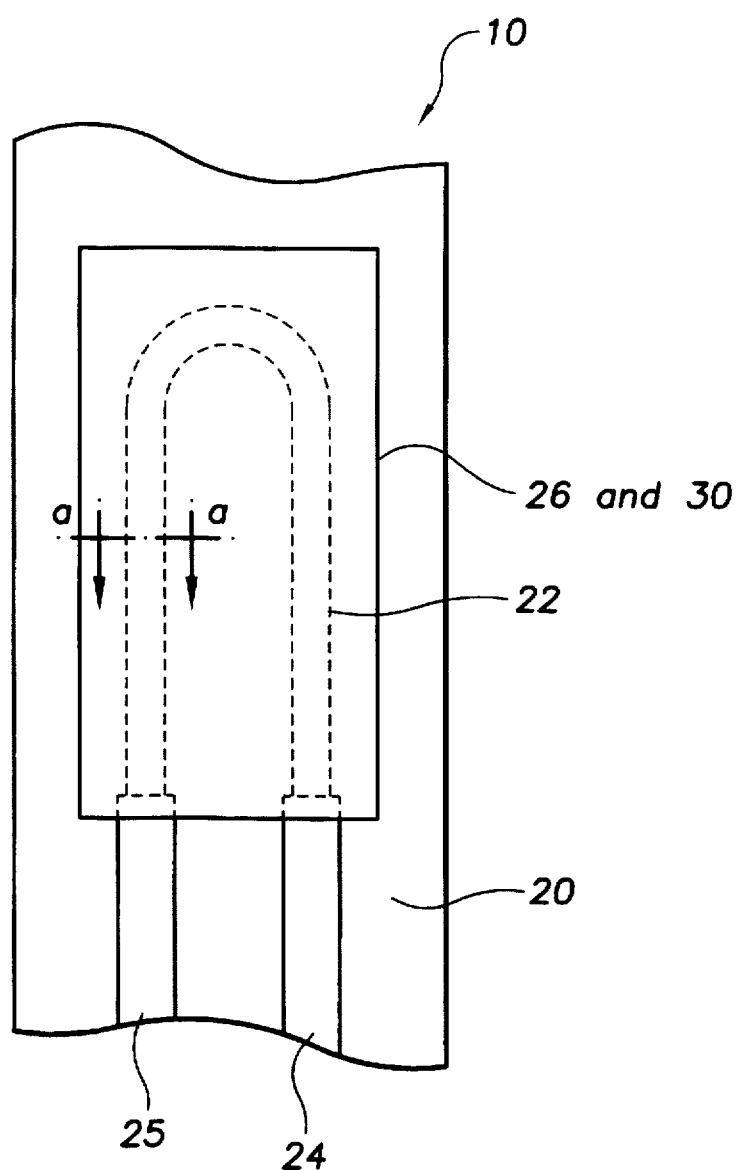
FIG. 1 is a plan view showing the sensor of the present invention.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements between the drawings.

DETAILED DESCRIPTION OF THE PREFERRED EMBODIMENT

The present invention provides a gas sensor having a compounded catalytic structure. The structure is ideally suited to sensing hydrocarbons and nitrogen oxides in an automobile exhaust system. Regarding FIG. 1, there is a plan view of the gas sensor 10 of the present invention showing a portion of a substrate (base) 20. Substrate 20 is preferably made out of a ceramic material but other suitable dielectric materials may be utilized. Only the portion of substrate 20 containing a catalytic support structure 24 has been included in FIG. 1 and not the non-catalytic support structure section.

The remaining portion of substrate 20 can take on any desired configuration that will supply the necessary structural and thermal properties for the sensor. For instance, the structure must be strong enough to survive the shock and vibration attendant in an automobile exhaust system. In addition, the thermal properties must be such that any catalytic reactions occurring on catalytic support structure 24 can be detected by a thermally sensitive resistor element 22 located on substrate 20 (i.e. the substrate must not extract so much of the heat from the catalytic reaction that there is no resulting temperature increase in resistor element 22).

Located on substrate 20 and electrically connected to resistor element 22, are conductors 25 and 26. Conductors 25 and 26 are connected to circuitry (not shown) that can detect resistance changes and accompanying voltage drops along the length of resistor element 22.

Figure 2:
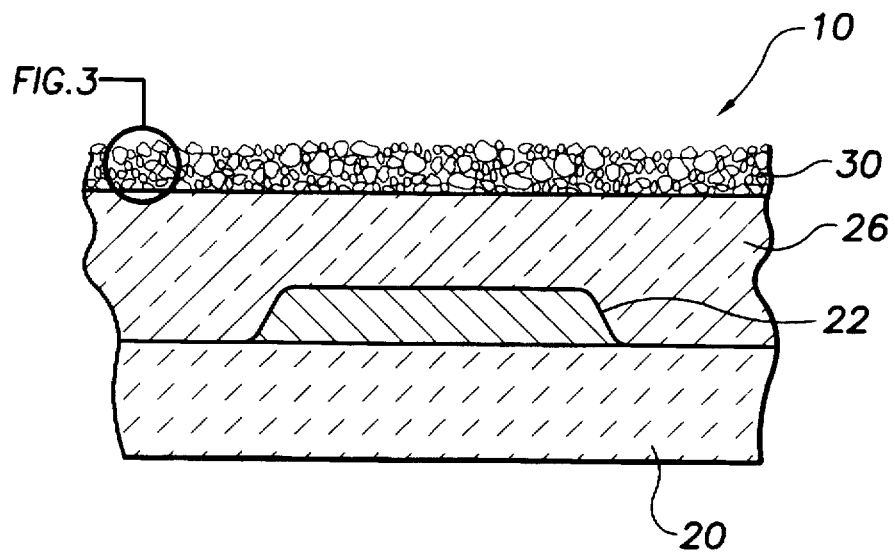
FIG. 2 is a cross-section of FIG. 1 taken through section a—a showing the compounded catalytic structure before firing.

In FIG. 2, a cross section taken through resistor element 22 is depicted. Resistor element 22 can be deposited on substrate 20 using any conventional thick or thin film technique as long as the deposit is robust enough to withstand the environment of an auto exhaust system and the thermal coefficient of resistivity is high enough so that the resistor will respond to temperature changes from catalytic reactions on the overlaid support structure. The material used to form resistor element 22 can be selected using these same criteria. In the preferred embodiment, it was found that platinum was a satisfactory material for resistor element 22 and that screen printing proved to be a suitable deposition method.

Conductors 24 and 25 can likewise be deposited using any conventional thick or thin film technique. Gold was selected as the conductor material for the preferred embodiment.

Figure 3:
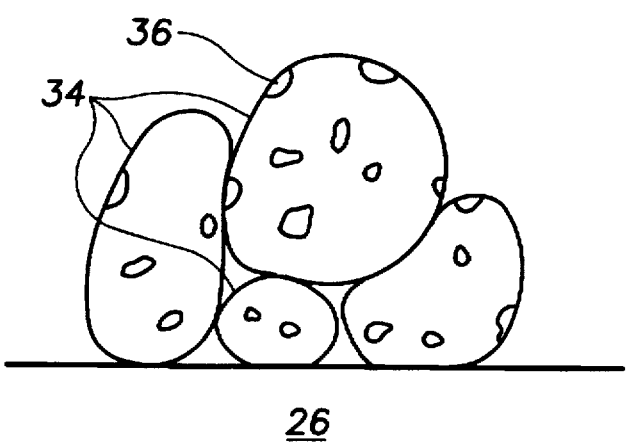
FIG. 3 is an enlargement of the circled portion of FIG. 2 showing greater detail of the catalyst support structure.

As shown in FIG. 2 and 3, the catalyst support structure 24, comprises a mixture of alumina particles 34 and powdered glass 32. In the preferred embodiment, the mixture includes 20% LaRoche V700 alumina and 80% GA-4 glass from Nippon Electric Glass. The alumina is calcined at about 600 degrees Centigrade for 1 hour before it is added to the mixture. This helps assure that the alumina will have a high surface area for a catalyst coating. Sufficient screening agent is added to the mixture to obtain a paste like consistency. The screening agent used in the preferred embodiment is comprised of an organic solvent, a rheology modifying solid and a wetting agent.

Figure 4:
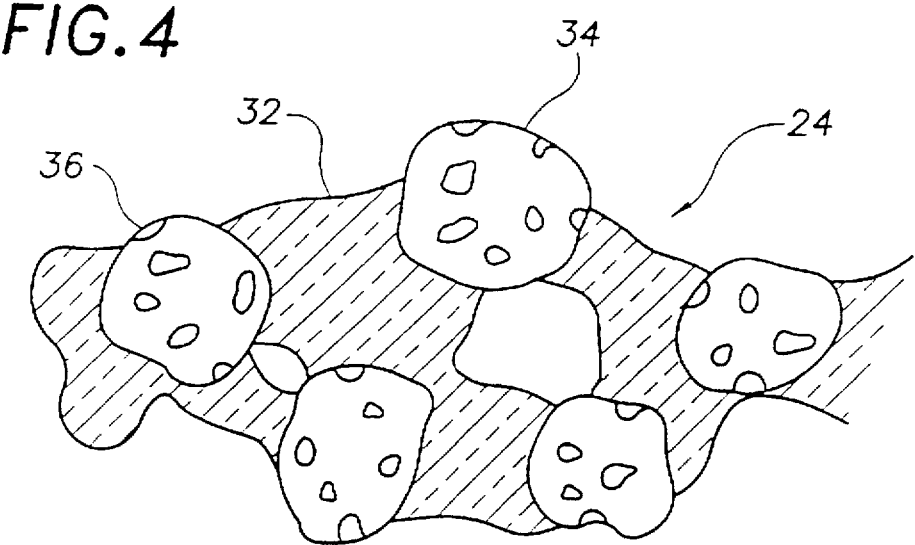
FIG. 4 shows what the structure of FIG. 3 looks like after it has been fired, and the glass has been reflowed.

The mixture is deposited over the resistor element 22. Screen printing is one suitable method of depositing the mixture; although it can also be deposited using a doctor blade, brushing etc. After catalytic support structure 24 is applied, the entire assembly is heated at a temperature that will reflow the glass employed. A temperature of 700 degrees centigrade for 1 hour is sufficient to reflow the GA-4 glass 32, and cause it to firmly adhere to both the alumina particles 34 and substrate 20 as shown in FIG.4. It is important that the glass bond very firmly to both the substrate and catalytic support because if the alumina particles flake off, the sensor will no longer function.

The final step is to apply a catalyst to catalytic support structure 30. In the preferred embodiment for a hydrocarbon sensor, platinum is used for the catalyst. The platinum is applied as a chloroplatinic acid solution using a dropper or other suitable technique. Afterwards the entire structure is reheated at a temperature that is high enough to reduce the acid to platinum. A temperature of 500 degrees centigrade was used for the preferred embodiment.

Alumina particles 34 vary in size and shape and the surface may include pores 36. When the chloroplatinic acid is applied and dried as described above, the surfaces of particles 34, including the surfaces of pores 36, will be covered by a very fine layer of platinum. Of course, some platinum will also adhere to the surfaces of glass 32.

Operation of the Sensor

The key to the operation of the sensor is the catalytic reaction of the gas to be sensed and the ability of the resistor element to respond to this respond to the reaction by a resulting change in its resistance. For example, as a hydrocarbon gas contacts the platinum catalyst, a chemical reaction occurs in which the hydrocarbon is combusted and heat is generated. The greater the quantity of hydrocarbons, the more heat is produced, thus causing the resistance of resistor element 22 to rise accordingly.

The resistance of resistor element 22 is then compared to the resistance of a reference sensor (not shown), which is in the same environment and of the same design, except that it is not covered with a catalyst. The difference in the resistance between resistor element 22 and the reference sensor (not shown) is due to the heat generated by the catalytic reaction. The resistance difference indicates the concentration of hydrocarbons in an exhaust stream.

Nitrogen Oxide Sensor Variation

A nitrogen oxide sensor can be made using the same procedure as outlined above for a hydrocarbon sensor except that a rhodium catalyst is substituted for platinum. The rhodium is deposited onto the catalytic support structure 24 in the form of rhodium chloride. The rhodium chloride is deposited in the same manner as the chloroplatinic acid and likewise heated to reduce the solution to pure rhodium.

Variations of the Preferred Embodiment

Although the illustrated embodiments depict the resistor element 22 in a horseshoe configuration one skilled in the art will realize that the gas sensor disclosed would work with other resistor patterns. The horseshoe shape merely provides an efficient means to place electrical conductors 25 and 26 in close proximity to each other for size constraints and manufacturability reasons.

In addition, the catalytic support structure 24 does not have to be applied in a rectangular shape as depicted in FIG. 1. It can be deposited in any desired shape. The same is true with the shape of substrate 20 as discussed above.

Furthermore, other types of ceramic particles besides alumina can be used in the catalytic support structure, and other glass materials besides GA-4 would also work with the invention. The glass content of the mixture can be varied from 40% to 90% with the remainder being ceramic particles. If the glass content is reduced below 40%, the mixture will not adhere properly to the base, and if the glass content exceeds 90%,then there will not be enough high surface area particles for holding the catalyst. Any glass that will adhere firmly to both the ceramic particles and substrate can be used. Additionally, other screening agents or water may be employed to make the mixture into a paste for deposition onto a substrate.

While the disclosure discusses the sensing of both hydrocarbon gas and nitrogen oxide, one skilled in the art of making gas sensors would easily adapt this design to sense most any gas that is capable of an exothermic reaction upon being exposed to a suitable catalytic material placed over the catalytic support structure.

Although the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by Letters Patent is:

1. A gas sensor for sensing the concentration of a gas, comprising:
   a) a base;
   b) a resistor element, located on the base, having an electrical resistance that changes based on a change in temperature of the resistor element;
   c) a compound catalyst support structure, including a mixture of ceramic particles and melted glass that binds the ceramic particles together and adheres the support structure to the base and resistor element; and
   d) a catalyst, located on both the melted glass and ceramic particles of the catalyst support structure, for promoting an exothermic reaction of the gas, thereby increasing the temperature of the resistor element.

2. The gas sensor of claim 1, wherein the base comprises ceramic.

3. The gas sensor of claim 2, wherein the ceramic comprises alumina.

4. The gas sensor of claim 1, wherein the catalyst includes platinum for causing a catalytic reaction when exposed to hydrocarbons.

5. The gas sensor of claim 1, wherein the catalyst includes rhodium for causing a catalytic reaction when exposed to nitrogen oxides.

6. The gas sensor of claim 1, wherein the ceramic particles are high surface area alumina particles.

7. The gas sensor of claim 6, wherein the high surface area alumina particles contain pores having a catalyst layer covering portions of the pores surface.

8. The gas sensor of claim 1, further comprising, conductors located on the base and electrically connected to the resistor element.

9. The gas sensor of claim 8, wherein the conductors are comprised of gold.

10. The gas sensor of claim 1, wherein the compound catalytic structure ranges from 20% alumina particles and 80% powdered glass to 60% alumina particles and 40% powdered glass.

11. A method for manufacturing a gas sensor, comprising:
   a) supplying a base having a thermally sensitive resistor element thereon;
   b) applying a mixture of ceramic particles and powdered glass to the base for use as a catalyst support structure;
   c) heating the base and catalyst support structure at a temperature that will reflow the glass to bind the ceramic particles together and adhere the catalyst support structure to the base;
   d) applying after step c), a catalyst in solution onto exposed surfaces of both the ceramic particles and reflowed glass of the catalyst support structure; and
   e) reheating the base and catalyst support structure after step e) to reduce the catalyst in solution to a pure catalyst.

12. The method of claim 11, wherein the base is comprised of ceramic.

13. The method of claim 12, wherein the ceramic includes alumina.

14. The method of claim 11, wherein the ceramic particles are alumina having a high surface area.

15. The method of claim 14, wherein the alumina particles are calcined prior to being mixed with powdered glass.

16. The method of claim 11, wherein the mixture ranges from 20% ceramic particles and 80% powdered glass to 60% ceramic particles and 40% powdered glass.

17. The method of claim 16, wherein the ceramic particles are alumina.

18. The method of claim 11 wherein the catalyst is platinum for initiating reactions with hydrocarbons.

19. The method of claim 11, wherein the catalyst is rhodium for initiating reactions with nitrogen oxides.

20. The method of claim 11, wherein the ceramic particles and powdered glass are mixed with a screening agent comprising an organic solvent, a rheology modifying solid, and a wetting agent to form a paste before application to the base.

21. The method of claim 11, wherein the heating temperature for reflowing the glass is 700 degrees centigrade.

22. The method of claim 11, further comprising, supplying the base with conductors electrically connected to the thermally sensitive resistor element.

23. The method of claim 22, wherein the conductors are comprised of gold.

24. The method of claim 11, wherein the powdered glass includes type GA-4 glass.

25. A method for manufacturing a gas sensor, comprising:
   a) supplying a base having a gold conductor electrically connected to a thermally sensitive resistor element thereon;
   b) calcining alumina particles at 600 degrees centigrade for one hour for the purpose of maintaining a high surface area;
   c) making a mixture comprising 20% alumina particles and 80% powdered glass;
   d) adding a screening agent comprising an organic solvent, a rheology modifying solid, and a wetting agent to the mixture to form a paste;
   e) screen printing the mixture on the base and over the resistor element for use as a catalyst support structure;
   f) heating the assembly at a temperature of 700 degrees centigrade to reflow the glass to bind together the alumina particles and adhere the mixture to the base;

g) applying, after step f), a catalyst solution onto exposed surfaces of both the alumina particles and reflowed glass of the catalyst support structure; and h) reheating, after step g), the assembly at 500 degrees centigrade to reduce the catalyst solution to a pure catalyst.

26. The method of claim 25, wherein the catalyst solution is platinic acid.

27. The method of claim 25 wherein the catalyst solution is rhodium chloride.

28. The method of claim 25, wherein the pure catalyst is platinum for initiating reactions with hydrocarbons.

29. The method of claim 25, wherein the pure catalyst is rhodium for initiating reactions with nitrogen oxides.

* * * * *